Figure 1:
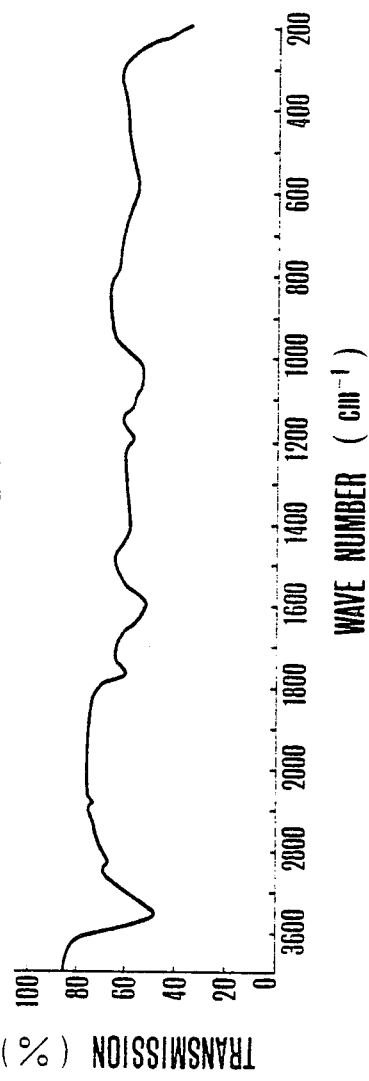

United States Patent [19]

Asano et al.

[11] 4,243,662

[45] Jan. 6, 1981

[54] PLANT-VIRUS CONTROLLING AGENT

[75] Inventors: Kiro Asano, Kukizaki; Tsuyoshi Saito, Tokyo; Masayoshi Hatanaka; Susumu Ikeda, both of Iwaki, all of Japan

[73] Assignee: Kureha Kagaku Kogyo Kabushiki Kaisha, Tokyo, Japan

[21] Appl. No.: 29,546

[22] Filed: Apr. 12, 1979

Related U.S. Application Data

[62] Division of Ser. No. 943,474, Sep. 18, 1978.

[30] Foreign Application Priority Data

Sep. 16, 1977 [JP] Japan ................................ 52-111968

[51] Int. Cl.$^3$ .......................... A61K 31/73; C07H 5/06
[52] U.S. Cl. ....................................... 424/180; 536/1; 536/18
[58] Field of Search ....................... 536/1, 18; 424/180

[56] References Cited

U.S. PATENT DOCUMENTS

| 3,436,311 | 4/1969 | Ferguson et al. | 536/1 |
| 3,759,896 | 9/1973 | Komatsu et al. | 536/1 |
| 4,140,578 | 2/1979 | Yoshikumi et al. | 536/1 |

Primary Examiner—Johnnie R. Brown
Attorney, Agent, or Firm—Stevens, Davis, Miller & Mosher

[57] ABSTRACT

A novel product comprising nitrogen-containing polysaccharides is produced by bringing a culture product of fungi Basidomycetes into reaction with an aqueous ammoniacal solution at a temperature of 100° to 250° C. The product is remarkably effective in controlling various plant viruses.

3 Claims, 2 Drawing Figures

PLANT-VIRUS CONTROLLING AGENT

This is a division of application Ser. No. 943,474 filed Sept. 18, 1978.

The present invention relates to a novel nitrogen-containing polysaccharides which is effective in protecting plants from the attack of various plant viruses.

It has been reported and discussed in "Plant Protection" Vol. 29, No. 1, pages: 17–19 (1975) that aqueous extracts of fungi Basidiomycetes are effective as a plant virus controlling agent. It is described in this reference that when various species of fungi Basidiomycetes were tested to determine their viral infection-inhibiting ability by a "mixing" method in which an aqueous extract of a fungus Basidiomycetes was mixed with a virus and then applied onto leaves of plants to be tested, the extracts of fruit bodies of 43 species of the fungi and those of cultured mycelia of 2 species of the fungi were found to exhibit an effective infection-inhibiting ability against tobacco mosaic virus (hereinlater abbreviated as TMV) and cucumber mosaic virus (hereinlater abbreviated as CMV). However, it is also described that no reliable inhibiting ability against viral infection was recognized when the extracts were applied onto the lower side of a leaf of which a virus had been inoculated on the upper side of leaves according to the test method of candidate anti-virus agent. Thus, in the case where a basidiomycete are applied as a plant virus-controlling agent, its antiviral component does not show any systemic action but acts on the viruses only on the same side of a leaf. Accordingly, these agents from Basidiomycetes exhibit little or no effect on so-called insect-mediated viruses which are the pathogens of plant virus diseases such as CMV disease, cucumber green mottled mosaic virus (hereinlater abbreviated as CGMMV) disease, CMV disease on pumpkin and the like which are mediated by insects such as aphids and where the particles of the viruses are directly injected into the plant body by these insects.

There is accordingly a strong demand for the development of plant virus-controlling agents which are able to prevent the occurrence of the systemic diseases due to plant viruses.

According to the present invention, it has now been found that a novel water-soluble product consisting of nitrogen-containing polysaccharide which is obtainable by causing reaction of a culture product of fungi Basidiomycetes with an aqueous ammoniacal solution at a temperature within a specific range under pressure exhibits a desirable systemic action in the plant body and the excellent antiviral activity.

The culture product of fungi Basidiomycetes used as the starting material in the practice of the present invention means mycelia, fruit bodies and cultures of these fungi, extracts obtained by extracting these mycelia, fruit bodies and cultures with water, and extraction residues thereof. Of these, the extraction residue gives the best results when used as the starting material. Aqueous solvents for the extraction are, for example, water or aqueous solutions of acids or alkalies.

Fungi Basidiomycetes are not particularly restricted to the species but good results are obtained especially when fungi belonging to the genus Coriolus of Polyporaceae of Aphyllophorales and the genus Lentinus of Tricholomataceae of Agaricales are used.

The term "fungi Basidiomycetes" as used herein is based on the classification in "Colored Illustration of Fungi of Japan" Vols. I and II by Rokuya Imazeki and Tsugio Hongo (Hoikusha Pub. Co.).

The above-mentioned nitrogen-containing polysaccharide can be produced by treating a culture product of the above-mentioned fungi with aqueous ammoniacal solution at a temperature of 150°–250° C., under pressure corresponding to the vapor pressure of the aqueous ammoniacal solution at the temperature of the reaction in a pressure-vessel such as a batch-type autoclave or in a continuous reactor or extractor. Moreover, in the case where an extraction residue of mycelia, fruit bodies or cultures of these fungi is utilized as the starting material, the temperature at which the above-mentioned heat-treating is carried out is preferably 190° to 230° C. In the reaction, a reaction accelerator such as, for example, $(NH_4)_3PO_4$ may be added to the system. The concentration of the charged aqueous ammoniacal solution is in the range of 0.03–17 N, preferably 0.5–10 N. The reaction period may vary depending on the temperature applied and is generally in the range of 5 minutes to 12 hours, preferably in the range of 4–10 hours at a temperature in the above range. The reaction may be carried out repeatedly on the same material under the above-indicated conditions.

On completion of the reaction, the reaction product is filtered after cooling and the excess of ammonia is neutralized or evaporated. If necessary, the filtrate is subjected to ultrafiltration, salting-out, dialysis, reverse osmosis or a combination thereof to purify the effective component, followed by concentrating or drying to obtain a nitrogen-containing polysaccharide.

The product obtained in the manner described above has the following physicochemical properties:

Range of Molecular Weight

500–10,000

Color Reactions

The product is positive in $\alpha$-naphthol-sulfuric acid reaction, phenol-sulfuric acid reaction, Elson-Morgan reaction (for glycosamine) Lowry-Forlin reaction (for peptide linkage) and ninhydrin reaction (for protein and amino acids).

Elementary Analysis

Though more or less varying depending on the species of Basidiomycetes or the extraction conditions when the extract or extraction residue is used as the starting basidiomycetous material, the above-mentioned polysaccharide contains, as determined by elementary analysis, 38–50% of carbon, 2.5–10% of nitrogen, and 5.5–7.5% of hydrogen.

Infrared Absorption Spectrum

Figure 2:
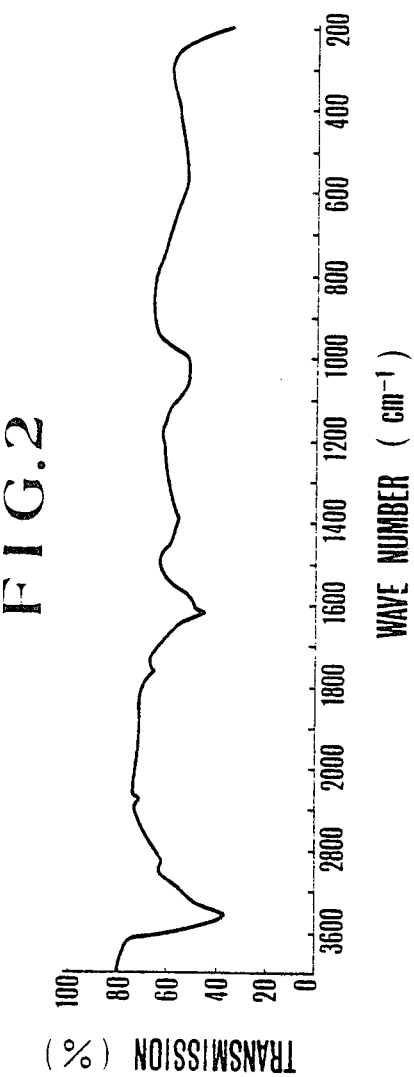

As shown in FIGS. 1 and 2 of the accompanying drawings, the infrared absorption spectrum of the product according to the present invention indicates a far larger absorption in the vicinity of 1620 cm$^{-1}$ as compared with that of the reference material (see FIG. 1).

From the above, it has been found that the product of the invention is a nitrogen-containing polysaccharide or a mixture thereof. It may be assumed in view of its larger nitrogen content than that of the nitrogen-containing polysaccharide merely extracted from the fungus with water or an aqueous alkaline solution indicated above that the product is a reaction product of the nitrogen-containing polysaccharides in the fungi and ammonia. The product of the present invention is considered to have nitrogen-containing groups such as —NH₂, —CONH₂, —COONH₄ and the like, introduced by the reaction with ammonia. It is assumed that the product exhibits such an antiviral activity and a systemic action in the plant body as a result of introduction of the above-mentioned radicals and linkages. The product of the present invention is readily soluble in water.

When applied as a plant virus-controlling agent, the product of the invention is used as an aqueous solution. The product of the present invention may be mixed with ordinary auxiliary materials such as, spreaders, dispersing agents and the like. The product may be used in combination with other agricultural chemicals or fertilizers in certain cases.

The plant virus-controlling agent according to the present invention may be sprayed on to the leaves, stems of the plants to be protected or applied to their roots. By the application, the agent will be effectively absorbed in the plant body by its systemic action thereby to effectively control the viral diseases.

The plant virus controlling agent of the present invention is very advantageous from a practical point of view in that it exhibits no phytotoxicity to the applied plants.

The present invention will be particularly described by way of the following examples.

EXAMPLE 1

The cultured mycelia of a strain of *Coriolus versicolor* (Fr.) Quel. (FERM-P No. 2413) of Polyporaceae was brought into reaction with aqueous amminiacal solutions of different concentrations to investigate the relationship between the reaction conditions such as reaction period, temperature, etc. and the antiviral activity of the reaction product. The antiviral activity was determined as follows:

*Cucumis sativus* (variety: Kinsei Santo) or *Nicotiana tabacum* (variety: KY-57, and bright yellow) was used as test plants and the CMV, TMV and CGMMV were used as viruses. In the examination test, one leaf of the test plant to be inoculated with a virus was sacked with a pouch made of plastic film to avoid the contact of the leaf with the test liquid. Then, the test liquid containing the product of the present invention was sprayed over the plant and allowed to stand for 3 hours for drying. The pouch was removed and the virus to be tested was inoculated into the leaf by the carborundum method. The inoculum of the virus was a 1:2,000 dilution of a pressed juice from infested leaves by the virus for the CMV, a 1:10,000 dilution for the TMV, and a 1:5,000 dilution for the CGMMV, respectively. The number of the test plants was ten per test plot. The tested plants were checked after 2 weeks of the inoculation as to whether they showed viral symptoms or not, and the antiviral activity was indicated in terms of a disease inhibiting rate $$(1 - \frac{A}{B}) \times 100 \ (\%),$$

where A is the number of the plants on which any viral symptom was oberved, and B is the total number of the plants used in the respective test.

Preparation of starting material (cultured mycelia of *Coriolus versicolor* (Fr.) Quél.):

A strain of *Coriolus versicolor* (Fr.) Quél. (strain FERM-P No. 2413) was shake-cultured in a liquid medium (pH 6.5) having a composition consisting of 3 g of peptone, 5 g of yeast extract, 10 g of malt extract, 20 g of glucose, 0.1 g of potassium primary phosphate, 0.1 g of potassium secondary phosphate, 0.05 g of magnesium sulfate heptahydrate and 1 l of water contained in a rotary shaker of 200 rpm at 26° C. for 170 hours. After completion of the culture, the mycelia were collected by filtration, washed with distilled water, and dried at 80°–100° C. for 48 hours to obtain the dried mycelia.

One hundred grams of the thus obtained mycelia (having a moisture content of 12% and a nitrogen content of 3%) and 1,200 g of aqueous ammoniacal solution of different concentrations as indicated in Table 1 were charged into an autoclave, heated under agitation from room temperature up to 150° C. in one hour, and kept at the temperature for a predetermined period for reaction. After cooling, the reactant was filtered and the filtrate from which the insoluble matters had been removed was heated to 80° C. and maintained at the temperature under reuced pressure for 3 hours to drive out the excess ammonia. After cooling, the filtrate was subjected to the ultrafiltration under a pressure of 4 kg/cm² to collect the substance with molecular weight larger than 500. The collected fraction was dried under reduced pressure to obtain the product.

Characteristics of the Product

The color reactions of the thus obtained product were determined by usual manner. As a result, it was found that the product was positive in α-naphthol-sulfuric acid reaction, phenol-sulfuric acid reaction, Elson-Morgan reaction, Lowry-Forlin reaction, and ninhydrin reaction.

In order to obtain the conception concerning the molecular weight of the product, the product was dialised, and the content of fractions having molecular weight below 10,000 was expressed percentage by weight.

The infrared absorption spectrum of the product revealed, as clearly seen from FIGS. 1 and 2, that the absorption in the vicinity of 1620 cm⁻¹ was larger than that of a reference substance which was obtained by extracting the dried mycelia with water alone. From the above finding, it has been confirmed that the product according to the present invention was a reaction product of the starting material, mycelia of the basidiomycete, and ammonia. In FIGS. 1 and 2 there are shown the infrared absorption spectra of the reference substance of Test No. 15 (Comparative Example) and the substance of Test No. 4 (Example of the present invention) as typical examples of such spectra.

The antiviral activity of the product obtained in the manner described above was determined as follows.

*Nicotiana tabacum* (variety: KY-57) was used as a test plant and at first inoculated with CMV, to which were applied the products to be tested each at a concentration of 1,000 ppm to determine their antiviral activity.

The yield, chemical characteristics and antiviral activity of the products obtained under different reaction conditions such as reaction temperature, concentration of aqueous ammonia and reaction period are summarized in Table 1.

TABLE 1

| Test No. | Reaction Conditions concentration of charged aqueous ammoniacal solution(N) | reaction temp. (°C.) | reaction period (hr) | Purified Product Yield (% by weight) | Nitrogen content (%) | Antiviral activity (%) | Remarks |
|---|---|---|---|---|---|---|---|
| 1 | 1 | 100 | 6 | 20 | 3.0 | 40 | Comparative experiment |
| 2 | 1 | 130 | 6 | 32 | 3.5 | 60 | " |
| 3 | 1 | 150 | 6 | 52 | 4.5 | 90 | Example of present invention |
| 4 | 1 | 180 | 6 | 68 | 5.8 | 100 | Example of present invention |
| 5 | 1 | 200 | 6 | 70 | 5.9 | 100 | Example of present invention |
| 6 | 1 | 250 | 6 | 52 | 5.9 | 90 | Example of present invention |
| 7 | 0.5 | 250 | 6 | 50 | 4.3 | 90 | Example of present invention |
| 8 | 5 | 150 | 6 | 60 | 7.0 | 100 | Example of present invention |
| 9 | 7 | 150 | 6 | 62 | 7.1 | 100 | Example of present invention |
| 10 | 1 | 200 | 4 | 68 | 5.3 | 100 | Example of present invention |
| 11 | 1 | 200 | 10 | 73 | 8.5 | 100 | Example of present invention |
| 12 | 0 (water) | 100 | 6 | 18 | 1.0 | 20 | Comparative experiment |
| 13 | 0 (water) | 130 | 6 | 27 | 1.0 | 10 | " |
| 14 | 0 (water) | 150 | 6 | 32 | 0.8 | 0 | " |
| 15 | 0 (water) | 180 | 6 | 35 | 0.6 | 0 | " |
| 16 | — | — | — | — | — | 0 | Inoculated, but not applied |

As will be clearly seen from Table 1, any of the effective substances of the invention show excellent antiviral activity.

EXAMPLE 2

One hundred and fifty grams of the dried mycelia (having a moisture content of 12%) with a nitrogen content of 3.0% of *Coriolus versicolor* (Fr.) Quel. (FERM-P No. 2413) obatined in the same manner as in Example 1 was subjected to extraction with 2 l of water at 100° C. for 6 hours and the residue was removed by filtration to obtain an extract. A concentrated aqueous ammoniacal solution was added to the filtered extract to make the normality of ammonia in the mixture to unity and the mixture was heated 150° C. and kept at the temperature for 6 hours in an autoclave. Then, the solution was cooled and treated as in Example 1 to obtain 30 g of a powder. The content, in the powder, of fractions with a molecular weight below 10,000 was found to be 73% by weight and its nitrogen content was 5.0%.

The antiviral activity of the powder was determined by using *Nicotiana tabacum* (variety: bright yellow) for TMV, *Cucumis sativus* (variety: Kinsei Santo) for CGMMV, and both plants (variety: Kinsei Santo), (variety: KY-57) for CMV.

The results of the antiviral activity test for different concentrations of the powder are shown in Table 2.

TABLE 2

| Test No. | Concentration of the powder in the applied solution (ppm) | type of virus | plant used for test | anti-viral activity (%) | Remarks |
|---|---|---|---|---|---|
| 1 | 1000 | CMV | tobacco (KY-57) | 80 | example of the present invention |
| 2 | 500 | CMV | tobacco (KY-57) | 70 | example of the present invention |
| 3 | 100 | CMV | tobacco (KY-57) | 60 | example of the present invention |
| 4 | 0 | CMV | tobacco (KY-57) | 0 | reference |
| 5 | 100 | TMV | tobacco (bright yellow) | 80 | example of the present invention |
| 6 | 0 | TMV | tobacco (bright yellow) | 0 | reference |
| 7 | 100 | CGMMV | cucumber | 80 | example of the present invention |
| 8 | 0 | CGMMV | cucumber | 0 | reference |
| 9* | 100 | CMV | tobacco (KY-57) | 20 | comparative example |

*The substance used in the test No. 9 is that which was obtained by extracting the mycelia of *Coriolus versicolor* with hot water at 100° C. for 6 hours by a known technique.

From Table 2, it will be understood that the substance of the present invention are excellent in antiviral activity.

EXAMPLE 3

Fifty grams of the extraction residue obtained in Example 2 was heated together with 2 N aqueous ammoniacal solution in an autoclave at a temperature of 200° C. for 6 hours. The reaction product was filtered and the filtrate was treated for purification as in Example 1 to obtain 30 g of powder. The content, in the powder, of fractions with molecular weights below 10,000 was 85% and the nitrogen content was 5.2%.

The antiviral activity of the powder against CMV was determined by using *Nicotiana tabacum* as a test plant (variety: KY-57) with the results shown in Table 3.

TABLE 3

| Test No. | Concentration of the powder in the applied solution (ppm) | Anti-viral activity (%) |
|---|---|---|
| 1 | 500 | 100 |
| 2 | 100 | 80 |
| 3 (reference) | 0 | 0 |

As will be clearly seen from the Table 3, the product of the present invention are excellent in antiviral activity.

EXAMPLE 4

A strain of *Coriolus consors* (Fr.) Quél. (strain FERM-P No. 988) of the family Polyporaceae was shake-cultured at 25° C. for 7 days in a liquid medium with a composition of 30 g of glucose, 3 g of yeast extract, 0.3 g of potassium primary phosphate, 1 g of ammonium sulfate, and 1 l of water. Ammonia was then added to the resulting culture until the concentration of ammonia reached 2.5 N, followed by charging the mixture into an autoclave for reaction at 230° C. for 8 hours. After completion of the reaction, the reaction product was cooled to about 100° C. and then air was blown into the product thereby evaporating excess of ammonia in the product. Then, the product was allowed to cool and filtered. The filtrate was subjected to ultrafiltration to remove fractions with molecular weights below 500 from the filtrate and it was dried under reduced pressure to obtain 3.5 g of a powder which had a nitrogen content of 5.8% and a content of fractions with molecular weights below 10,000 and more than 500 of 90%. The powder was applied as an aqueous solution to *Nicotiana tabacum* (variety: KY-57) in different concentrations to determine its antiviral activity against CMV with the results shown in Table 4.

TABLE 4

| concentration of the powder in the applied solution (ppm) | 1000 | 500 | 100 | 50 | 0 |
|---|---|---|---|---|---|

TABLE 4-continued

| Anti-viral activity (%) | 100 | 90 | 80 | 60 | 0 |
|---|---|---|---|---|---|

EXAMPLE 5

One hundred grams of each of dry fruit bodies of the following basidiomycetes were cut into pieces: commercially available *Pholiota nameko* (belonging to the family Strophariaceae of the order Agaricales), *Lyophyllum aggregatum* (belonging to the family Tricholomataceae of the order Agaricales), *Lentinus edodes* (belonging to the family Tricholomataceae of the order Agaricales) and *Tricholoma matsutake* (belonging to the family Tricholomataceae of the order Agaricales), and *Lactarius piperatus* (belonging to the family Russulaceae of the order Agaricales), *Mycena galericulata* (belonging to the family Tricholomataceae of the order Agaricales) and *Coriolus versicolor* (belonging to the family Polyporaceae of the order Aphyllophorales), the latter three being collected in the mountains of Iwaki City, Fukushima Prefecture.

Each 100 g of the above-mentioned cut specimens was placed in an autoclave together with 1.2 l of 5 N aqueous ammoniacal solution for reaction at 150° C. for 6 hours. After completion of the reaction, the reaction product was cooled and filtered to remove insoluble matters therefrom. The filtrate was heated up to 80° C. under reduced pressure to remove an excess of ammonia for 5 hours. Each filtrate was treated as in Example 1 to obtain a purified powder. Each of the thus obtained powderes was subjected to determination of its nitrogen content, yield, content of fractions with molecular weights below 10,000, and an infrared absorption at 1620 cm$^{-1}$.

Further, the antiviral activity of each powder against CMV was determined by the use of *Nicotiana tabacum* as in Example 1. The results are summarized in Table 5.

TABLE 5

| Species of fruit bodies | characteristics of purified product | | | Concentration of the product in the applied solution (ppm) | Anti-viral activity (%) |
|---|---|---|---|---|---|
| | Yield (% by weight) | Nitrogen content (%) | presence of infrared absorption at 1620 cm$^{-1}$ | | |
| *Pholiota nameko* | 12 | 4.0 | yes | 500 | 40 |
| *Lyophyllum aggregatum* | 24 | 4.5 | yes | 500 | 40 |
| *Lentinus edodes* | 30 | 3.8 | yes | 500 | 50 |
| *Lentinus edodes* | 30 | 3.8 | yes | 100 | 40 |
| *Tricholoma matsutake* | 24 | 4.5 | yes | 500 | 60 |
| *Lactarius piperatus* | 24 | 5.8 | yes | 500 | 50 |
| *Coriolus versicolor* | 35 | 6.2 | yes | 500 | 80 |
| *Coriolus versicolor* | 35 | 6.2 | yes | 100 | 70 |
| *Mycena galericulata* | 18 | 4.2 | yes | 500 | 60 |

EXAMPLE 6

A mycelial mat of *Lentinus edodes* (FERM-P No. 1757) was inoculated into a malt soup medium in a 300-ml Erlenmeyer flask and static-cultured for 15–20 days. The static-cultured mycelia were homogenized to be used as a seed-culture. The thus obtained seed-culture was inoculated in an aqueous medium (pH 5.0) having a composition indicated in Table 6, and the cultivation of the fungus was carried out to obtain the mycelia as follows:

TABLE 6

| Component | Amount (g/l) | Component | Amount (g/l) |
|---|---|---|---|
| glucose | 50 | $FeCl_2 \cdot 6H_2O$ | 0.01 |
| peptone | 2.5 | $MnCl_2 \cdot 4H_2O$ | 0.0072 |
| yeast extract | 2.5 | $ZnCl_2$ | 0.004 |
| $KH_2PO_4$ | 1.0 | $CuSO_4 \cdot 5H_2O$ | 0.001 |
| $MgSO_4 \cdot 7H_2O$ | 0.5 | Water | A volume to make the total volume of the culture medium to be one liter. |
| $CaCl_2 \cdot 2H_2O$ | 0.5 | | |

Aliquots of 100 ml of the above-mentioned aqueous medium were introduced into 60 shaking flasks (500 ml), respectively; 3 ml of the seed-culture were inoculated to each of the aliquots and the fungus was shake-cultured at an amplitude of 7 cm and at 100 r.p.m. for 4 days. The resulting culture was separated by filtration and dried to obtain 30 g of mycelia (with a moisture content of 15%). Fifteen grams the dried mycelia and 200 g of 1 N aqueous ammoniacal solution were charged into an autoclave and heated at 180° C. for 6 hours and then the reaction product was treated as in Example 1 to obtain 8.9 g of a dried powder (having a nitrogen content of 3.6% and a content of components with molecular weights below 10,000 of 74% by weight). The infrared absorption spectroscopy on the powder revealed the new appearance of an absorption in the vicinity of 1620 $cm^{-1}$.

For comparative purpose, 15 g of the dried mycelia and 200 g of water instead of aqueous ammoniacal solution were charged into an autoclave, followed by treating in the same manner described above to obtain 7.5 g of a dried powder (having a nitrogen content of 1.0% and a content of components with molecular weights below 10,000 of 70% by weight).

Each of the powders was applied as an aqueous solution at a concentration of 1000 ppm to Nicotiana tabacum (variety: KY-57) in the same manner as in Example 1 to obtain its antiviral activity. As a result, it was found that the antiviral activity of the mycelia treated with 1 N aqueous ammoniacal solution (according to the present invention) was 70%, while that of the mycelia treated with water (comparative example) was 0%.

EXAMPLE 7

One hundred grams of dried mycelia of Coriolus versicolor (Fr.) Quél. (strain FERM-P No. 2413) were introduced into an antoclave containing 1,200 g of aqueous 14% ammoniacal solution (normality of about 8), and the content of the autoclave was heated from room temperature to 200° C. at a heating rate of 150° C.,/hr under agitation and kept at the temperature for 5 hours. After cooling, the treated material was filtered to remove the undissolved matter, and unreacted ammonia still remaining in the filtrate was driven off by heating the filtrate to 80° C. under reduced pressure. After cooling, the thus treated filtrate was subjected to ultrafiltration to collect the fractions (a) with molecular weight range of 500–10,000 and (b) with molecular weight over 10,000. The fractions were obtained by drying the filtrates thus subjected to ultrafiltration and they were named Specimen A (mol. wt. 500–10,000) and Specimen B (mol. wt. over 10,000).

Another 100 g of dried mycelia of the same fungus as above were treated by nearly the same technique as mentioned above, however, the heat-treatment was carried out for 3 hours at 180° C. After removing the undissolved matter and unreacted ammonia by the same technique as mentioned above, the thus treated filtrate was subjected to ultrafiltration to collect the fraction with molecular weight larger than 10,000. The fraction was obtained by drying the filtrate thus subjected to ultrafiltration for collecting that of molecular weight larger than 10,000, and it was named Specimen C.

Antiviral activity of the two Specimens A, B and C was determined by using Nicotiana tabacum (Variety: KY-57) as the test plant and using TMV as the test virus. Thirty plants were at first inoculated with an inoculum of TMV (a 1:10,000 dilution of pressed juice of infested leaves of Nicotiana tabacum, and then 10 plants were treated by spraying of an aqueous solution of Specimen A at a concentration of 500 ppm. Another 10 plants were treated by spraying of an aqueous solution of Specimen B at a concentration of 500 ppm.

Still another 10 plants were treated by spraying of a aqueous solution of Specimen C at a concentration of 500 ppm.

Antiviral activity of the specimen was represented by the plant virus disease inhibiting rate (%) calculated by the followng formula:

$$(1 - \frac{X}{10}) \times 100 (\%),$$

where X represents the number of plants on which any symptom of TMV disease was found at the observation after 2 weeks of the inoculation. The figure 10 means the number of total plants inoculated and treated with the spray.

The results of the test showed that in the plot where Specimen A was sprayed, the plant virus disease inhibiting rate (antiviral activity) was 90(%), whereas, in the plot where Specimen B was sprayed, the plant virus disease inhibiting rate (anti-viral activity) was only 10(%) and in the plot where Specimen C was sprayed, the plant virus disease inhibiting rate (anti-viral activity) was substantially zero.

What is claimed is:

1. A method of protecting a plant from infection by a plant virus of the group consisting of tobacco mosaic virus, cucumber mosaic virus and cucumber green mottled mosaic virus, which comprises treating a plant of the species belonging to the Solanaceae family or to the Cucurbitaceae family with an aqueous solution of a product consisting essentially of nitrogen-containing polysaccharides having the elementary composition of 38 to 50% carbon, 2.5 to 10% nitrogen, 5.5 to 7.5% of hydrogen, the balance being oxygen, having a molecular weight between 500 and 10,000 and showing a characteristic infrared absorption band at about 1620 $cm^{-1}$, obtained by bringing a culture product of Basidiomycetes fungus into reation with an aqueous ammoniacal solution of a normality of 0.03 to 17 N, at a temperature of 150° to 250° C., under pressure of said aqueous ammoniacal solution at said reaction temperature by filtering the reaction product to obtain a filtrate and then, after purifying said filtrate, by drying said purified filtrate.

2. A method according to claim 1, wherein the aerial part of said plant to be protected from the infection by said plant viruses is treated by spraying an aqueous solution of said product at a concentration of 100 to 1000 ppm.

3. A method according to claim 1, wherein the root system of said plant to be protected from infection by said plant virus is treated by soaking in an aqueous solution of said product at a concentration of 100 to 1000 ppm or spraying such aqueous solution thereon.

* * * * *